(12) United States Patent
Zimmer et al.

(10) Patent No.: US 12,318,322 B2
(45) Date of Patent: Jun. 3, 2025

(54) ORTHOPEDIC NECK BRACE WITH SLIDING PIVOT CHIN SUPPORT

(71) Applicant: Aspen Medical Products, LLC, Irvine, CA (US)

(72) Inventors: Erik Zimmer, Oceanside, CA (US); Jozsef Horvath, Fullerton, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 719 days.

(21) Appl. No.: 16/774,828

(22) Filed: Jan. 28, 2020

(65) Prior Publication Data

US 2021/0228396 A1   Jul. 29, 2021

(51) Int. Cl.
  *A61F 5/055*   (2006.01)
  *F16C 11/04*   (2006.01)

(52) U.S. Cl.
  CPC .............. *A61F 5/055* (2013.01); *F16C 11/04* (2013.01)

(58) Field of Classification Search
  CPC ........ A61F 5/055; A61F 5/05883; A61F 5/05; A61F 5/04; A61F 5/01; A61F 5/56
  USPC ........................................... 602/18
  See application file for complete search history.

(56) References Cited

U.S. PATENT DOCUMENTS

| | | | |
|---|---|---|---|
| 2,791,999 A | 5/1957 | Bustamante | |
| 5,005,563 A | 4/1991 | Veale | |
| 5,501,646 A | 3/1996 | Miller | |
| 5,688,229 A | 11/1997 | Bauer | |
| 5,865,773 A | 2/1999 | Koledin | |
| 6,423,020 B1 | 7/2002 | Koledin | |
| 7,674,234 B2 * | 3/2010 | Calco | A61F 5/055 602/18 |
| 7,748,384 B2 | 7/2010 | Ho et al. | |
| 9,913,746 B2 | 3/2018 | Martin et al. | |
| 2003/0093019 A1 | 5/2003 | Bonutti | |
| 2004/0204666 A1 | 10/2004 | Marsh | |
| 2013/0104903 A1 | 5/2013 | Matula, Jr. et al. | |
| 2013/0281899 A1 * | 10/2013 | Suarez | A61F 5/055 602/18 |
| 2013/0281900 A1 * | 10/2013 | Suarez | A61F 5/055 602/18 |
| 2016/0008158 A1 | 1/2016 | Martin et al. | |

(Continued)

FOREIGN PATENT DOCUMENTS

| CN | 205494105 U | 8/2016 |
|---|---|---|
| CN | 206304012 U | 7/2017 |

(Continued)

OTHER PUBLICATIONS

PCT/US2021/013576 filed Jan. 15, 2021 International Search Report and Written Opinion dated May 7, 2021.

(Continued)

*Primary Examiner* — Victoria Hicks Fisher
(74) *Attorney, Agent, or Firm* — Rutan & Tucker, LLP

(57) ABSTRACT

An orthopedic neck brace has right and left sliding pivots that couple a torso rest with a chin support. Over a wide range from relatively long necks to relatively short necks, the sliding pivots tend to raise and lower the chin piece vertically, which automatically keeps the chin support at a right angle to the rest of the brace, and prevent undesirable sagittal offsets. Preferred embodiments combine the sliding pivots with a rack and pinion neck height adjustment mechanism.

25 Claims, 6 Drawing Sheets

(56) References Cited

U.S. PATENT DOCUMENTS

2019/0015245 A1 1/2019 Vaidya
2020/0368056 A1* 11/2020 Doty ................... A61F 5/05883

FOREIGN PATENT DOCUMENTS

CN        207506674 U      6/2018
WO        WO9938466 A1    12/1899
WO        2015108576       7/2015

OTHER PUBLICATIONS

EP21747967.4 filed Aug. 26, 2022, Extended European Search Report dated Jan. 22, 2024.

* cited by examiner

ORTHOPEDIC NECK BRACE WITH SLIDING PIVOT CHIN SUPPORT

The field of the invention is orthopedic neck brace.

BACKGROUND THE INVENTION

The following description includes information that may be useful in understanding the present invention. It is not an admission that any of the information provided herein is prior art or relevant to the presently claimed invention, or that any publication specifically or implicitly referenced is prior art.

An orthopedic neck brace typically has at least three main components, a neck support, a chin support, and a coupling between the neck and chin supports. For ease of construction and adaptation to multiple neck widths, the neck support often comprises separable anterior (front) and posterior (back) components.

One of the most popular cervical collars, U.S. Pat. No. 7,674,234 to Calco, accommodates different neck lengths using a gear mechanism that raises and lowers the chin support with respect to the neck support. The chin support of the '234 device, however, is coupled to the neck support using a simple pivot that does not sufficiently accommodate cupping of the chin for particularly long or short necks. In particular, the simple pivot mechanism tends to push the chin piece posteriorly for long necks.

US20030093019B1 to Bonutti attempts to resolve these problems by providing for both vertical and sagittal adjustments. However, sagittal adjustments must be made manually, using a thumb screw. Accordingly, for particularly long or short necks, the brace must be manually adjusted in both vertical and sagittal directions.

A much earlier device, described in U.S. Pat. No. 5,501,646 to Miller, provides a chin support that does accommodate continuous, automatic, vertical and movements of the chin support. However, that design does so by mounting the chin support on a spring arm extending upwards from the wearer's torso, which allows excessive movement in both vertical and sagittal directions.

All of these publications are incorporated by reference to the same extent as if each individual publication were specifically and individually indicated to be incorporated by reference. Where a definition or use of a term in an incorporated reference is inconsistent or contrary to the definition of that term provided herein, the definition of that term provided herein applies and the definition of that term in the reference does not apply.

There is still a need for an orthopedic neck brace that provides a chin support that maintains a proper sagittal positioning of the chin support piece, to maximize the contact surface between it and the patient's chin, over a wide range of neck lengths.

SUMMARY OF THE INVENTION

The inventive subject matter provides an orthopedic neck brace that uses a sliding pivot mechanism to couple a chin support to a front neck piece, maintaining a proper sagittal positioning of the chin support piece over a wide range of neck lengths. Preferred orthopedic braces utilize two sliding pivot mechanisms, one to the right of the chin support, and one to the left of the chin support.

The sliding pivot mechanism is preferably coupled to a height adjustment mechanism, such that operation of the height adjustment mechanism automatically operates the sliding pivot mechanism.

In preferred embodiments the chin support is carried by right and left intermediate members, which are in turn carried by right and left side members, respectively. On each side, the sliding pivot mechanism comprises a pin that is simultaneously, slidably disposed within both a slot of the side member and a slot of the corresponding intermediate member.

Two subtypes of sliding mechanisms are described herein. In one subtype the right and left side members are further coupled to their corresponding right and left intermediate members by additional sliding pivots, and another subtype the right and left side members are further coupled to their corresponding right and left intermediate member by pivoting arms and non-sliding (simple) pivots. In both cases the axes of the two pivoting attachments of the chin piece reside perpendicular to the sagittal plane, which cooperate to raise or lower the chin piece vertically, regardless of neck length. This accommodates the contour of the chin/mandible as the collar height adjustment is set, and reduces otherwise potential edge pressures by interface/anatomic misalignment.

As used herein, the term "slot" means any manner of race, including an elongated hole or indentation, in which a pin or button can travel along a constrained path.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides example embodiments of the inventive subject matter. Although each embodiment represents a single combination of inventive elements, the inventive subject matter is considered to include all possible combinations of the disclosed elements. Thus, if one embodiment comprises elements L, L, and C, and a second embodiment comprises elements R and D, then the inventive subject matter is also considered to include other remaining combinations of L, L, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Figure 1:
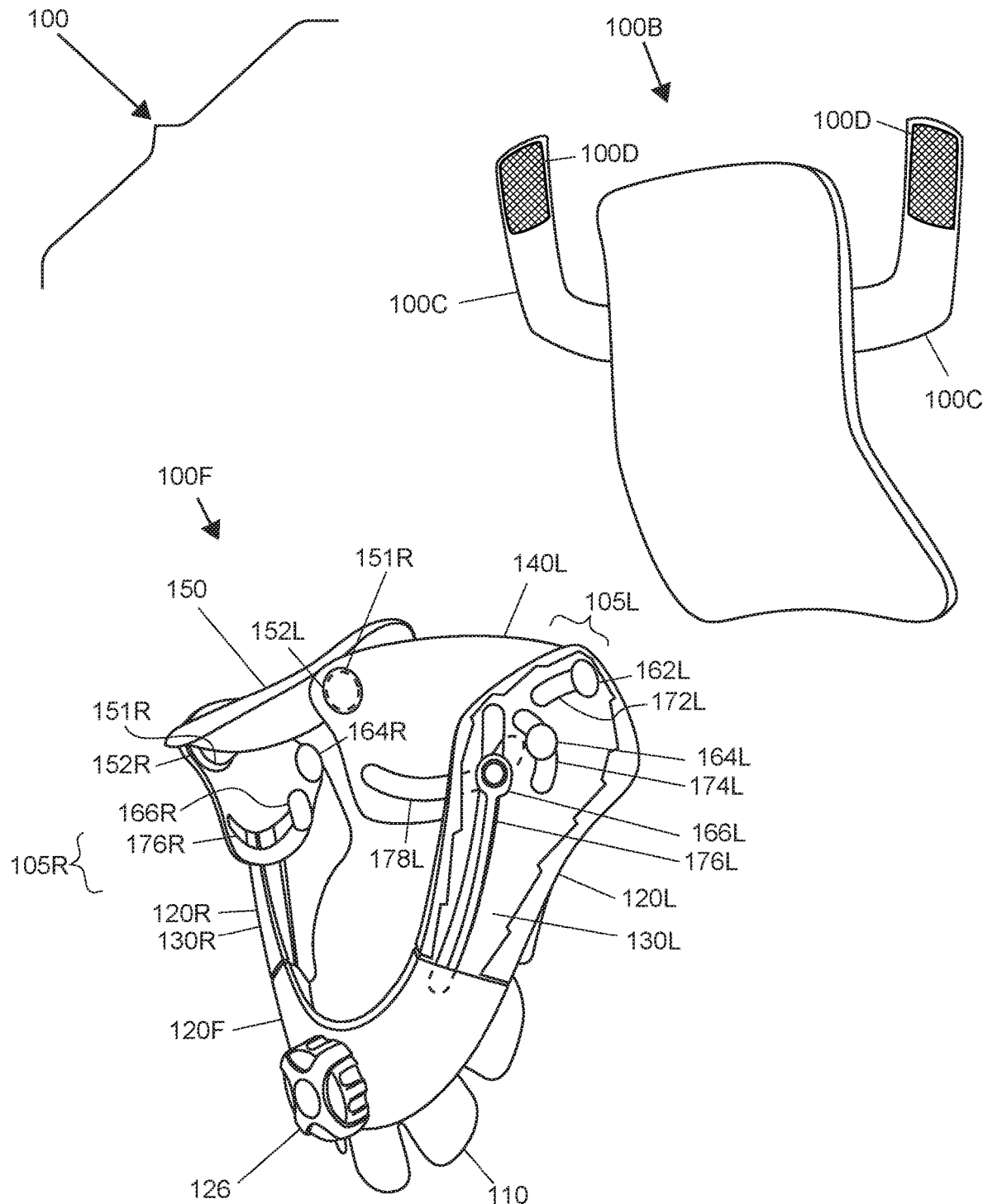
FIG. 1 is a perspective view of an orthopedic brace according to the inventive subject matter, showing both front and back pieces.

FIG. 1 depicts an orthopedic brace 100 comprising a front piece 100F and a back piece 100B, which can be coupled together via arms 100C using a hook and loop fasteners 100D. The terms "left" and "right" in this application refer to components from the standpoint of a person wearing the brace.

The front piece 100F generally comprises a torso rest 110, front cover 120F, right cover 120R, left cover 120L, a height control knob 126 that forms part of a height adjustment mechanism 125, right and left side members 130R, 130L, and a chin support 150. The right side member 130R is coupled to the chin support 150 using pin 151R extending through hole 152R in the right intermediate member 140R. The left side member 130L is coupled to the chin support 150 using pin 151L extending through hole 152L in the left intermediate member 140L. Pins 151R, 151L are preferably sized and dimensioned with respect to the corresponding holes 152R, 152L such that sagittal (anterior-posterior) movement between the chin support 150 and the intermediate pieces 140R, 140L is preferably limited to no more than 3 mm, more preferably to no more than 2 mm, and still more preferably to no more than 1 mm.

The height adjustment mechanism 125 is described in detail in U.S. Pat. No. 7,674,234 to Calco et al, which is incorporated herein in its entirety, and is further described with respect to FIG. 2B below.

As used herein, the term "torso rest" means that portion of a neck brace through which weight is transmitted to the torso region of a person who is properly wearing the brace.

The front piece 100F of orthopedic neck brace 100 has right and left sliding pivot mechanisms 105R, 105L, which concurrently move the right intermediate member 140R relative to right side member 130R, and the left intermediate member 140L relative to left side member 130L. This arrangement of sliding pivot mechanisms cooperate to provide essentially vertical movement of the chin piece during neck length adjustments, i.e., without undesirable sagittal offsets.

Figure 2A:
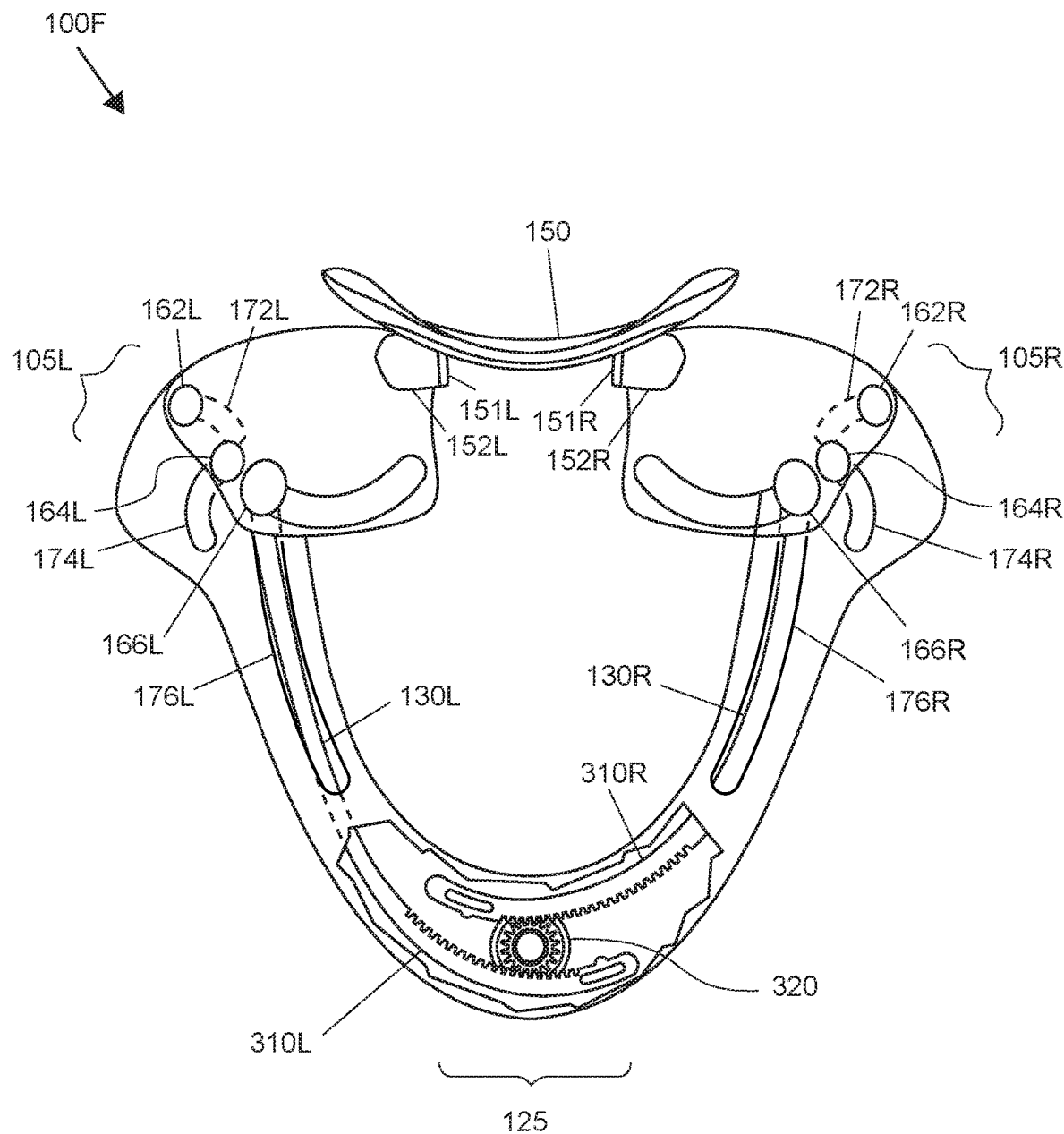
FIG. 2A is a cutaway rear view of the front piece of FIG. 1, configured for a long neck.

As better visualized in FIG. 2A, the sliding pivot mechanism 105R is accomplished, on the right side, using first, second, and third pins 162R, 164R, and 166R, which are configured to slide within slots 172R, 174R, and 176R, respectively. In this particular example, slots 172R, 174R, and 176R are all formed or cut into the right side member 130R, and the first and second pins 162R, 164R are positionally fixed with respect to the right intermediate member 140R. There is a fourth slot 178R formed or cut into the right intermediate member 140R, and pin 166R slides concurrently within both slot 176R of the right side member 130R and slot 178R in the right intermediate member 140R.

The left side is similar. The sliding pivot mechanism 105L is accomplished using first, second, and third pins 162L, 164L, and 166L, which are configured to slide within slots 172L, 174L, and 176L, respectively. In this particular example, slots 172L, 174L, and 176L are all formed or cut into the left side member 130L, and the first and second pins 162L, 164L are positionally fixed with respect to the left intermediate member 140L. There is a fourth slot 178L formed or cut into the left intermediate member 140L, and pin 166L slides concurrently within both slot 176L of the left side member 130L and slot 178L in the left intermediate member 140L.

Figure 2B:
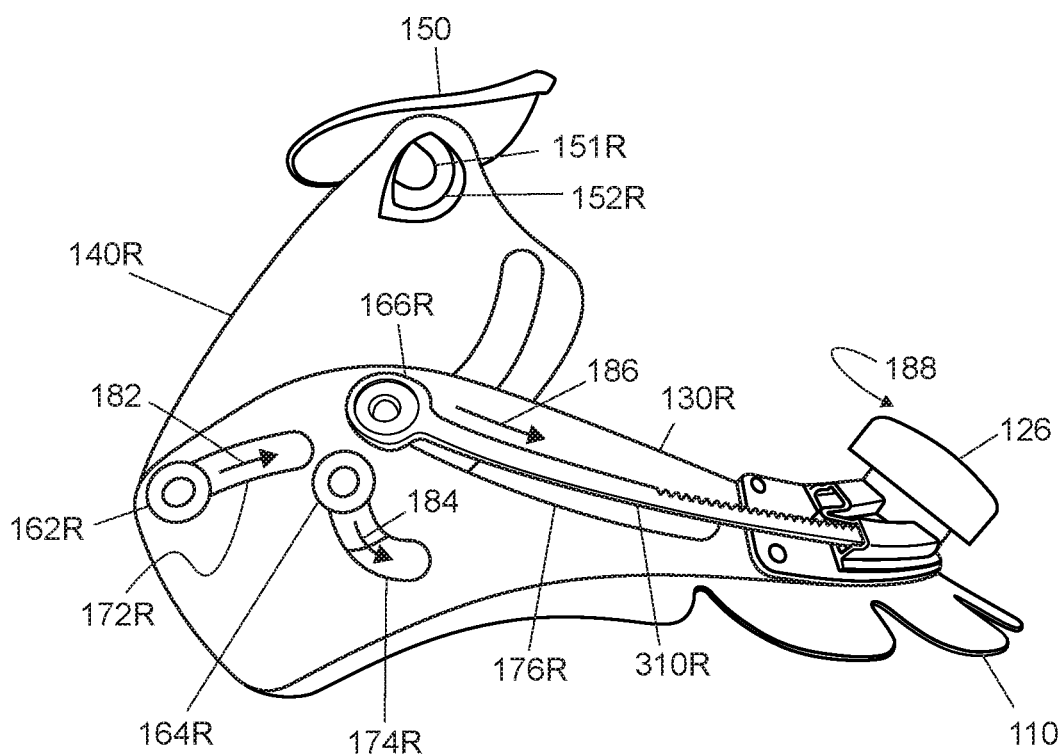
FIG. 2B is a cutaway right side view of the front piece of FIG. 1, configured for a long neck as in FIG. 2A.
Figure 2C:
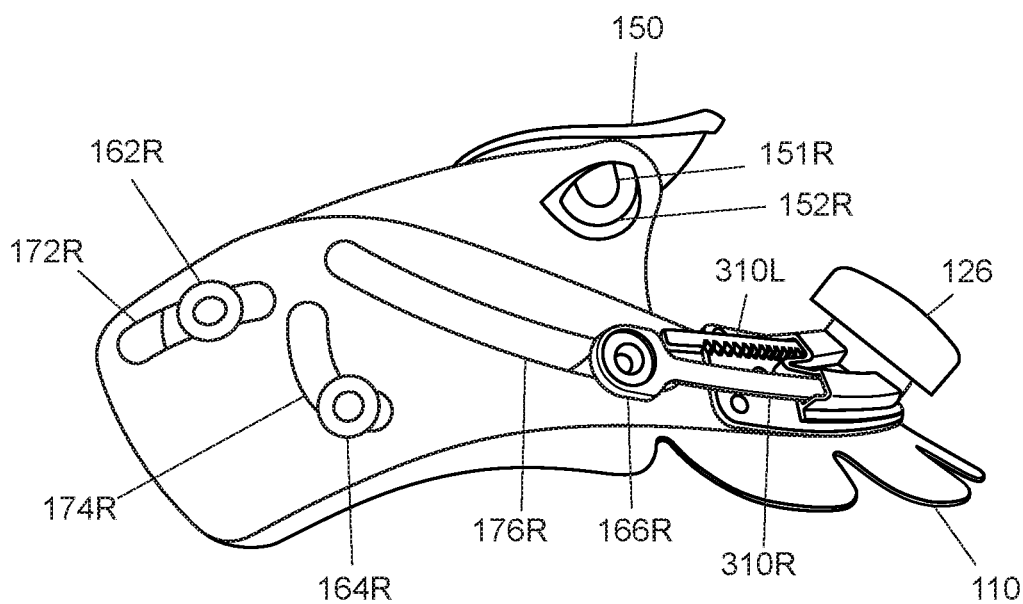
FIG. 2C is a cutaway right side view of the front piece of FIG. 1, configured for a short neck.

FIG. 2A depicts a partial cutaway of a rear view of the front piece 100F of orthopedic neck brace 100, as configured for a long neck. FIGS. 2B and 2C depict components from the same brace, but from a right side view. FIG. 2B depicts such components configured for a long neck, and FIG. 2C depicts such components configured for a short neck. FIG. 2B additionally depicts three arrows 182, 184, 186 that show motion of the first, second, and third pins 162R, 164R, and 166R, respectively, in reconfiguring the front piece 100F of brace 100 from the long neck configuration of FIGS. 2A and 2B, to the short neck configuration of FIG. 2C. Concurrently with such motions, height control knob 126 is rotated counterclockwise, as shown by arrow 188. As used herein, the terms "counterclockwise" and "clockwise" should be interpreted as viewed from the front of the front piece 100F.

Returning specifically to FIG. 2A, the height adjustment mechanism 125 generally comprises right and left racks 310R, 310L, which cooperate with pinion 320 to move right and left side pins 166R, 166L, respectively, farther from or closer to pinion 320. Height control knob 126 is configured to both rotate pinion gear 320, and optionally to lock pinion gear 320 in place. Additional details can be found in U.S. Pat. No. 7,674,234 to Calco et al, referenced above.

The height adjustment mechanism 125 operates the sliding pivot mechanism 105R (right side) because pin 166R is fixedly positioned with respect to the right rack 310R. Turning the height control knob 126 counterclockwise moves pin 166R from a higher position in slot 176R to a lower position in slot 176R, along arrow 186, which moves pin 166R forward along slot 178R, which moves both right intermediate member 140R and chin support 150 downwardly (inferiorly) and forward (anteriorly).

Similarly, the height adjustment mechanism 125 operates the sliding pivot mechanism 105L (left side) because pin 166L is fixedly positioned with respect to the left rack 310L.

Turning the height control knob 126 counterclockwise moves pin 166L from a higher position in slot 176L to a lower position in slot 176L, which moves pin 166L forward along slot 178L, which moves both left intermediate member 140L and chin support 150 downwardly and forwards (inferiorly and anteriorly on a wearer).

Turning the control knob 126 in a clockwise direction performs the opposite function, moving chin support 150 upwards and backwards (superiorly and posteriorly on a wearer).

Figure 3:
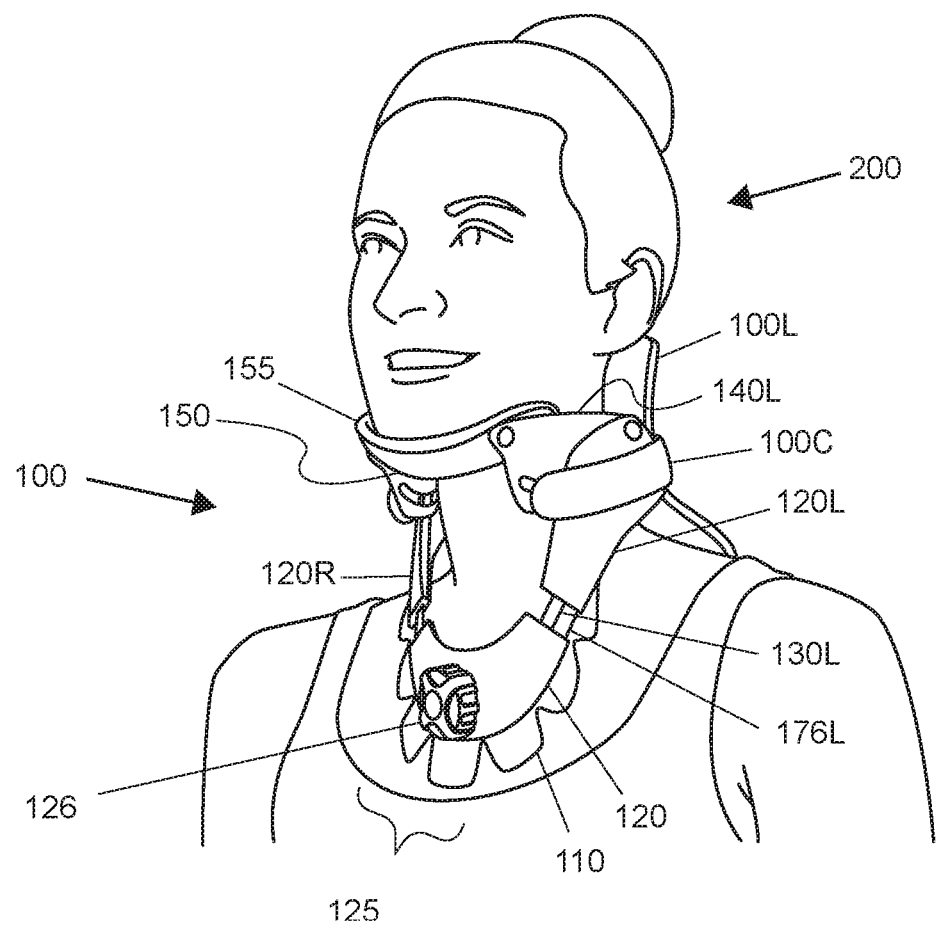
FIG. 3 is a schematic of the orthopedic brace of FIG. 1 being worn by a person.

In FIG. 3 the orthopedic neck brace 100 is being worn by a person 200. The height adjustment mechanism 125 (of which only the height control knob 126, and short sections of right track 310R and left track 310L, are visible) has been operated to accommodate the longer neck of the person, by distancing the front member 120 from the side members 130R, 130L. A foam pad 155 is present between the person's chin and the chin support 150.

All components of the orthopedic neck brace 100 except the torso rest 110, foam pad 155 fitted on the chin support 150, and the flexible coupling arms 100C, can advantageously be made of a hard thermoplastic or other sufficiently stiff, lightweight material. The torso rest 110 can advantageously be made from flexible high or low density plastics, including for example, nylon.

Figure 4A:
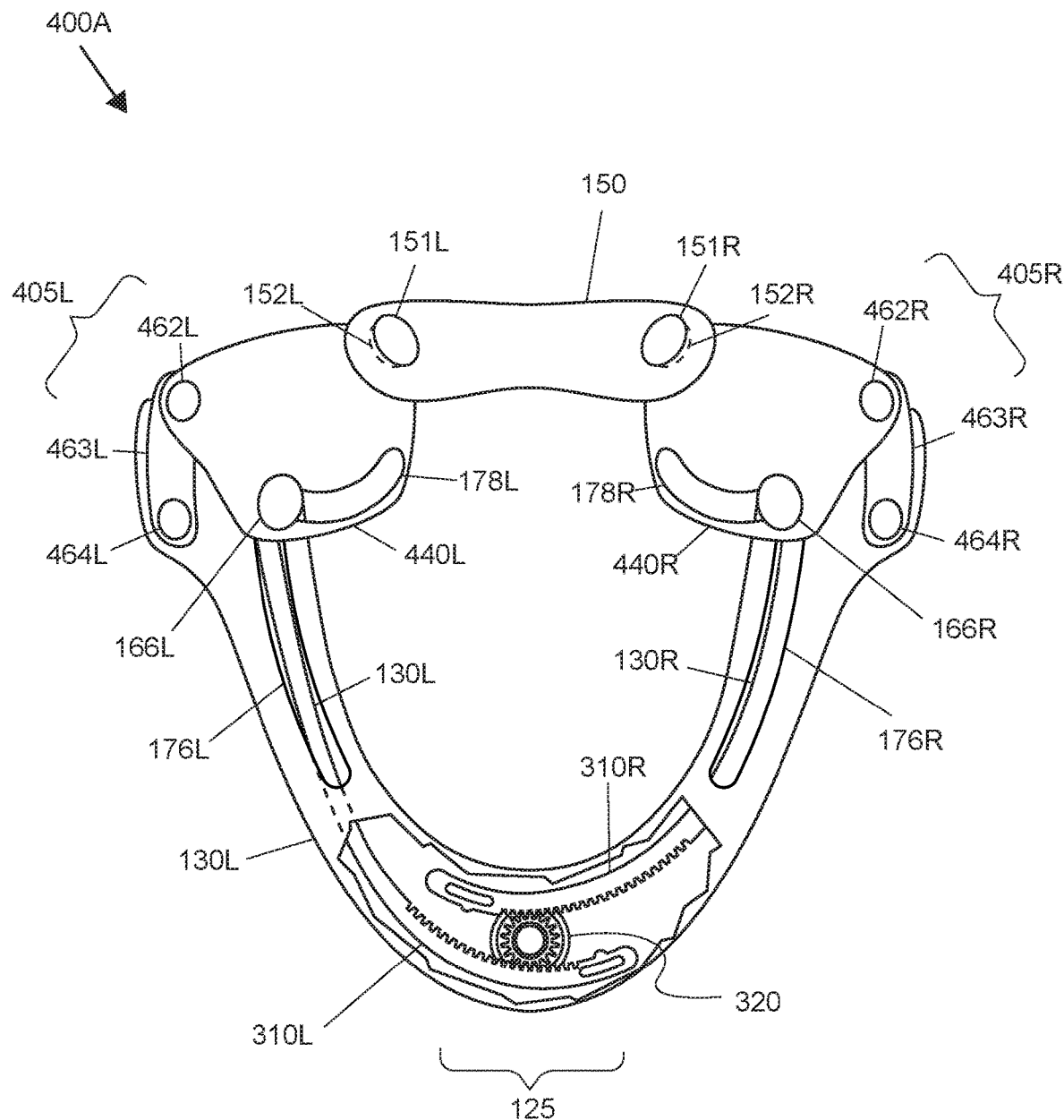
FIG. 4A is a cutaway rear view of the front piece of an alternative orthopedic neck brace, similar to that of FIG. 1, but with a different sliding pivot mechanism, and configured for a long neck.
Figure 4B:
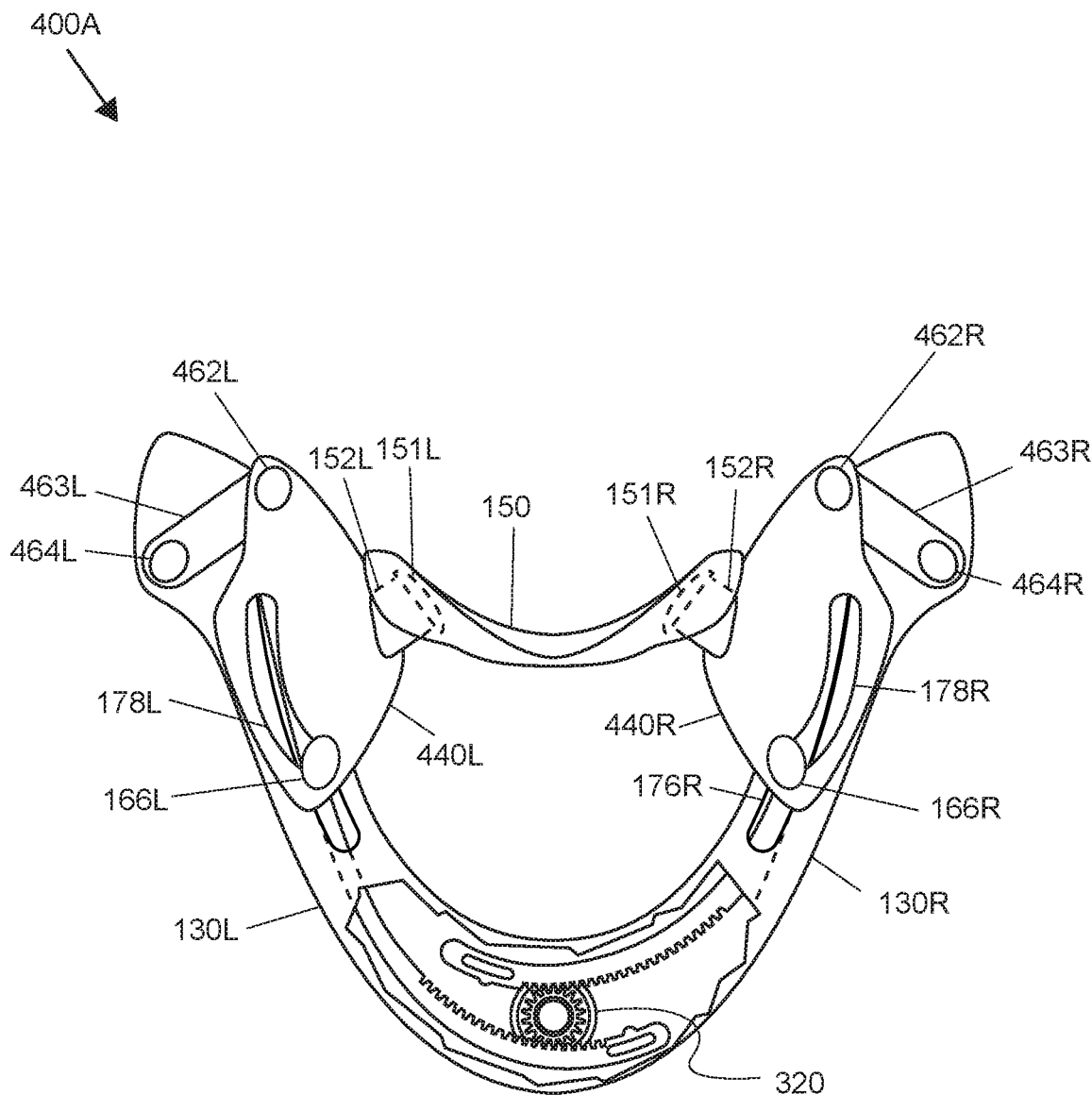
FIG. 4B is a cutaway rear view of the front piece of the alternative orthopedic neck brace of FIG. 4A, configured for a short neck.

In FIGS. 4A and 4B, the height mechanism the front piece 400A of an alternative orthopedic neck brace is similar to what is shown in FIGS. 1, 2A-2C, and 3, and is numbered correspondingly. Brace 400 includes lengthening/shortening knob (not shown) that cooperates with a pinion 320 to move and right and left racks 130R, 130L up and down. Those motions raise and lower pins 166R, 166L, which in turn raise and lower intermediate members 440R, 440L, which in turn raise and lower chin support piece 150.

The sliding pivot mechanisms, however, are different. In FIGS. 4A and 4B, the only sliding pins are right side pin 166R traveling concurrently in slots 176R and 178R, and left side pin 166L traveling concurrently in slots 176L and 178L. Instead of additional sliding pins, right and left intermediate members 440R, 440L are coupled to the right and left side members 130R, 130L, by rocker arms 463R, 463L, respectively. The right rocker arm 463R is rotatably coupled to the right intermediate member 440R using pin 462R, and is further rotatably to the right side member 130R using pin 464R. Similarly, the left rocker arm 463L is rotatably coupled to the left intermediate member 440L using pin 462L, and is further rotatably to the left side member 130L using pin 464L.

FIG. 4B depicts the same components as FIG. 4A, except that pinion 320 has been rotated counterclockwise to accommodate a shorter neck.

The sliding pivot mechanisms described herein are highly advantageous in that they tend to maintain the chin support at appropriate positioning, even when a brace is configured for relatively long or relatively short necks.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of L, L, C . . . and N, the text should be interpreted as requiring only one element from the group, not L plus N, or R plus N, etc.

What is claimed is:

1. An orthopedic neck brace comprising:
   a chin support;
   a first intermediate member coupled to a first side of the chin support, the first intermediate member includes a first slot extending in a first direction;
   a second intermediate member coupled to a second side of the chin support, the second intermediate member includes a second slot extending in a second direction different from the first direction;
   a first side member including a third slot extending in a first vertical direction and a fifth slot positioned adjacent to a first end of the third slot;
   a second side member including a fourth slot extending in a second vertical direction and a sixth slot positioned adjacent to a first end of the fourth slot;
   a first pin inserted through the first slot and the third slot for coupling the first intermediate member to the first side member;
   a second pin inserted through the second slot and the fourth slot for coupling the second intermediate member to the second side member;
   a third pin inserted through the fifth slot to further couple the first intermediate member to the first side member and provide a moveable pivot point for the first intermediate member;
   a fourth pin inserted through the sixth slot to further couple the second intermediate member to the second side member and provide a moveable pivot point for the second intermediate member; and
   a height adjustment mechanism including a height control knob that, upon rotation, causes (i) the first pin to move within both the first slot and the third slot, (ii) the second pin to move within both the second slot and the fourth slot, (iii) the third pin to move within the fifth slot, and (iv) the fourth pin to move within the sixth slot.

2. The orthopedic neck brace of claim 1, wherein
   a front piece including (i) the chin support, (ii) the first side member, (iii) the second side member, and (iv) the height adjustment mechanism; and
   a posterior piece coupled to the front piece by a hook and loop fastener.

3. The orthopedic neck brace of claim 1, wherein
   the first side member including the third slot being a curved slot functionally disposed between a torso rest and the chin support and the fifth slot being a curved slot functionality disposed between the third slot and an outer edge of the first side member, and
   the first intermediate member including the first slot being a curved slot functionally disposed between the first side member and the chin support.

4. The orthopedic neck brace of claim 3, wherein the second side member including the fourth slot being a curved slot functionally disposed between the torso rest and the chin support and the sixth slot being a curved slot functionally disposed between the fourth slot and an outer edge of the second side member, and
   the second intermediate member including the second slot being a curved slot functionally disposed between the second side member and the chin support.

5. The orthopedic neck brace of claim 1, wherein the height adjustment mechanism is configured to alter vertical movement of the chin support in relation to a torso rest during neck length adjustments without undesirable sagittal offsets.

6. The orthopedic neck brace of claim 1, wherein the chin support is moved upward and backward in response to a clockwise rotation of the height control knob.

7. The orthopedic neck brace of claim 1, wherein the second pin is moved downward along the fourth slot and inward along the second slot and the fourth pin is moved downward along the sixth slot in response rotation of the height control knob in a first rotational direction to cause downward movement of the chin support.

8. The orthopedic neck brace of claim 6, wherein the chin support is moved downward and forward in response to a counter-clockwise rotation of the height control knob.

9. The orthopedic neck brace of claim 1, wherein in response to rotation of the height control knob in a second rotational direction different than a first rotational direction, the first pin is moved upward along the third slot and outward along the first slot, the second pin is moved upward along the fourth slot and outward along the second slot, the third pin is moved along the fifth slot upward towards the third slot and the fourth pin is moved along the sixth slot upward towards the fourth slot to cause upward movement of the chin support.

10. The orthopedic neck brace of claim 1, wherein the height control knob cooperates with a pinion, a first rack coupled to the first pin, and a second rack coupled to the second pin.

11. The orthopedic neck brace of claim 10, wherein the rotation of the height control knob in a first rotational direction to cause counter-clockwise rotation of the pinion and downward movement of the first rack and the second rack and rotation of the height control knob in a second rotational direction different from the first rotational direction to cause clockwise rotation of the pinion and upward movement of the first rack and second rack.

12. An orthopedic neck brace comprising:
a chin support;
a plurality of intermediate members coupled to sides of the chin support, the plurality of intermediate members including a first intermediate member includes a first slot extending in a first direction and a second intermediate member includes a second slot extending in a second direction different from the first direction;
a plurality of side members includes (i) a first side member that comprises a third slot extending in a first vertical direction and a fifth slot positioned adjacent to a first end of the third slot and (ii) a second side member including a fourth slot extending in a second vertical direction and a sixth slot positioned adjacent to a first end of the fourth slot;
a first pin inserted through the first slot and the third slot for coupling the first intermediate member to the first side member;
a second pin inserted through the second slot and the fourth slot for coupling the second intermediate member to the second side member;
a third pin inserted through the fifth slot to further couple the first intermediate member to the first side member and provide a moveable pivot point for the first intermediate member;
a fourth pin inserted through the sixth slot to further couple the second intermediate member to the second side member and provide a moveable pivot point for the second intermediate member; and a height adjustment mechanism including a height control knob that, upon rotation, causes (i) the first pin to move within both the first slot and the third slot and (ii) the second pin to move within both the second slot and the fourth slot,
wherein the rotation of the height control knob of the height adjustment mechanism in a first rotational direction causes the first pin to be moved downward along the third slot and inward along the first slot that also causes movement of the chin support downwardly and forward to reduce a vertical height of the orthopedic neck brace and rotation of the height control knob of the height adjustment mechanism in a second rotational direction causes movement of the chin support upwardly and backward to increase the vertical height of the orthopedic neck brace.

13. The orthopedic neck brace of claim 12, wherein
a front piece including (i) the chin support, (ii) the first side member, (iii) the second side member, and (iv) the height adjustment mechanism; and
a posterior piece coupled to the front piece by a hook and loop fastener.

14. The orthopedic neck brace of claim 12, wherein the first side member including the third slot being a curved slot functionally disposed between a torso rest and the chin support and the first intermediate member including the first slot being a curved slot functionally disposed between the first side member and the chin support.

15. The orthopedic neck brace of claim 14, wherein the second side member including the fourth slot being a curved slot functionally disposed between the torso rest and the chin support and the second intermediate member including the second slot being a curved slot functionally disposed between the second side member and the chin support.

16. The orthopedic neck brace of claim 12, wherein the height adjustment mechanism is configured to alter vertical movement of the chin support in relation to a torso rest during neck length adjustments without undesirable sagittal offsets.

17. The orthopedic neck brace of claim 12, wherein the first pin is moved upward along the third slot and outward along the first slot in response to rotation of the height control knob in the second rotational direction to cause upward and backward movement of the chin support.

18. The orthopedic neck brace of claim 12, wherein the second pin is moved downward along the fourth slot and inward along the second slot in response the rotation of the height control knob in the first rotational direction to cause downward movement of the chin support.

19. The orthopedic neck brace of claim 18, wherein the chin support is moved downward and forward in response to the rotation of the height control knob in the first rotational direction corresponding to a counter-clockwise rotation of the height control knob.

20. The orthopedic neck brace of claim 12, wherein:
the height adjustment mechanism further comprises a pinion, a first rack coupled to the first pin, and a second rack coupled to the second pin, and
the first pin is moved upward along the third slot and outward along the first slot and the second pin is moved upward along the fourth slot and outward along the second slot in response rotation of the height control knob in the second rotational direction to cause clockwise rotation of the pinion and upward movement of the first rack and the second rack.

21. An orthopedic neck brace comprising:
a chin support;

a first intermediate member coupled to a first side of the chin support, the first intermediate member includes a first slot extending in a first direction;

a second intermediate member coupled to a second side of the chin support, the second intermediate member includes a second slot extending in a second direction different from the first direction;

a first side member including a third slot extending in a first vertical direction and a fifth slot positioned adjacent to a first end of the third slot;

a second side member including a fourth slot extending in a second vertical direction and a sixth slot positioned adjacent to a first end of the fourth slot;

a first pin inserted through the first slot and the third slot for coupling the first intermediate member to the first side member;

a second pin inserted through the second slot and the fourth slot for coupling the second intermediate member to the second side member;

a third pin inserted through the fifth slot to further couple the first intermediate member to the first side member and provide a moveable pivot point for the first intermediate member;

a fourth pin inserted through the sixth slot to further couple the second intermediate member to the second side member and provide a moveable pivot point for the second intermediate member; and a height control knob that, upon rotation, causes (i) the first pin to move within both the first slot and the third slot, (ii) the second pin to move within both the second slot and the fourth slot, (iii) the third pin to move within the fifth slot, and (iv) the fourth pin to move within the sixth slot.

22. The orthopedic neck brace of claim 21, wherein the first side member including the third slot being the curved slot functionally disposed between a torso rest and the chin support and the fifth slot being a curved slot functionality disposed between the third slot and an outer edge of the first side member.

23. The orthopedic neck brace of claim 22, wherein the second side member including the fourth slot being the curved slot functionally disposed between the torso rest and the chin support and the sixth slot being a curved slot functionality disposed between the fourth slot and an outer edge of the second side member.

24. The orthopedic neck brace of claim 21, wherein the height control knob cooperates with a pinion, a first rack coupled to the first pin, and a second rack coupled to the second pin and rotation of the height control knob in a first rotational direction to cause counter-clockwise rotation of the pinion, downward movement of the first rack and second rack and corresponding downward movement of the chin support while rotation of the height control knob in a second rotational direction to cause clockwise rotation of the pinion and upward movement of the first rack and second rack and corresponding upward movement of the chin support.

25. The orthopedic neck brace of claim 21, wherein the fifth slot is positioned adjacent to a first end of the third slot that is closer to the chin support than a second end of the fourth slot and the sixth slot is positioned adjacent to a first end of the fourth slot that is closer to the chin support than the second end of the fourth slot.

* * * * *